(12) United States Patent
Li et al.

(10) Patent No.: US 7,388,661 B2
(45) Date of Patent: Jun. 17, 2008

(54) NANOSCALE STRUCTURES, SYSTEMS, AND METHODS FOR USE IN NANO-ENHANCED RAMAN SPECTROSCOPY (NERS)

(75) Inventors: Zhiyong Li, Redwood City, CA (US); Zhaoning Yu, Mountain View, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 53 days.

(21) Appl. No.: 11/584,446

(22) Filed: Oct. 20, 2006

(65) Prior Publication Data

US 2008/0094621 A1   Apr. 24, 2008

(51) Int. Cl.
  *G01J 3/44* (2006.01)
  *G01N 21/65* (2006.01)
(52) U.S. Cl. ..................................... 356/301
(58) Field of Classification Search ................. 356/301
  See application file for complete search history.

(56) References Cited

U.S. PATENT DOCUMENTS

| | | | |
|---|---|---|---|
| 4,448,485 A * | 5/1984 | Bergman et al. ............ 359/328 |
| 4,512,848 A | 4/1985 | Deckman et al. |
| 4,674,878 A | 6/1987 | Vo-Dinh |
| 5,017,007 A | 5/1991 | Milne et al. |
| 5,255,067 A | 10/1993 | Carrabba et al. |
| 5,527,712 A | 6/1996 | Sheehy |
| 5,609,907 A | 3/1997 | Natan |
| 5,772,905 A | 6/1998 | Chou |
| 5,837,552 A | 11/1998 | Cotton et al. |
| 6,149,868 A | 11/2000 | Natan et al. |
| 6,165,911 A | 12/2000 | Calveley |
| 6,365,059 B1 | 4/2002 | Pechenik |
| 6,406,777 B1 | 6/2002 | Boss et al. |
| 6,432,740 B1 | 8/2002 | Chen |
| 6,623,977 B1 | 9/2003 | Farquharson et al. |
| 6,649,683 B2 | 11/2003 | Bell |
| 6,743,368 B2 | 6/2004 | Lee |
| 6,748,865 B2 | 6/2004 | Sakurai et al. |
| 6,755,984 B2 | 6/2004 | Lee et al. |

(Continued)

OTHER PUBLICATIONS

Collier, C.P., et al., "Reversible Tuning of Silver Quantum Dot Monolayers Through the Metal-Insulator Transition," Science, New Series, vol. 277, No. 5334, pp. 1978-1981, Sep. 26, 1997.

(Continued)

*Primary Examiner*—F. L Evans

(57) ABSTRACT

NERS-active structures for use in Raman spectroscopy include protrusions extending from a surface of a substrate. A Raman signal-enhancing material is disposed on at least one surface of a first protrusion and at least one surface of a second protrusion. The Raman signal-enhancing material disposed on the first protrusion projects laterally in a direction generally towards the second protrusion, and the Raman signal-enhancing material disposed on the second protrusion projects laterally in a direction generally towards the first protrusion. At least a portion of the Raman signal-enhancing projecting from the first protrusion and at least a portion of the Raman signal-enhancing material projecting from the second protrusion may be separated by a distance of less than about 10 nanometers. Raman spectroscopy systems include such NERS-active structures, and methods for performing Raman spectroscopy include irradiating an analyte proximate such a NERS-active structure and detecting Raman-scattered radiation scattered by the analyte.

28 Claims, 10 Drawing Sheets

U.S. PATENT DOCUMENTS

| | | |
|---|---|---|
| 6,759,180 B2 | 7/2004 | Lee |
| 6,829,988 B2 | 12/2004 | George et al. |
| 6,861,263 B2 | 3/2005 | Natan |
| 6,897,158 B2 | 5/2005 | Sharma |
| 6,916,511 B2 | 7/2005 | Lee et al. |
| 6,923,930 B2 | 8/2005 | Ling et al. |
| 6,975,891 B2 | 12/2005 | Pawluczyk |
| 7,080,596 B2 | 7/2006 | Lee et al. |
| 2003/0059820 A1* | 3/2003 | Vo-Dinh ............... 356/301 |
| 2004/0137734 A1 | 7/2004 | Chou et al. |
| 2005/0150404 A1 | 7/2005 | Lee et al. |
| 2006/0225162 A1* | 10/2006 | Yi ............... 977/754 |
| 2007/0086001 A1* | 4/2007 | Islam et al. ............... 356/301 |

OTHER PUBLICATIONS

Emory, Steven R., et al., "Screening and Enrichment of Metal Nanoparticles with Novel Optical Properties," J. Phys. Chem. B, vol. 102, No. 3, pp. 493-497, 1998.

Garcia-Vidal, F.J., et al., "Collective Theory for Surface Enhanced Raman Scattering," Physical Review Letters, vol. 77, No. 6, pp. 1163-1166, Aug. 5, 1996.

Kneipp, Katrin, et al., "Single Molecule Detection Using Surface-Enhanced Raman Scattering (SERS)," Physical Review Letters, vol. 78, No. 9, pp. 1667-1670, Mar. 3, 1997.

Michaels, Amy M., et al., "Surface Enhanced Raman Spectroscopy of Individual Rhodamine 6G Molecules on Large Ag Nanocrystals," J. Am. Chem. Soc., vol. 121, No. 43, pp. 9932-9939, 1999.

Nie, Shuming, et al., "Probing Single Molecules and Single Nanoparticles by Surface-Enhanced Raman Scattering," Science, New Series, vol. 275, No. 5303, pp. 1102-1106, Feb. 21, 1997.

Sun, L.F., et al., "Shawdow-evaporated nanometre-sized gaps and their use in electrical studies of nanocrystals," Nanotechnology, vol. 16, pp. 631-634, 2005.

Tao, Andrea, et al., "Langmuir-Blodgett Silver Nanowire Monolayers for Molecular Sensing Using Surface-Enhanced Raman Spectroscopy," Nano Lett., vol. 3, No. 9, pp. 1229-1233, 2003.

Wu, W., et al., "One-kilobit cross-bar molecular memory circuits at 30-nm half-pitch fabricated by nanoimprint lithography," Appl. Phys. A, vol. 80, pp. 1173-1178, 2005.

* cited by examiner

NANOSCALE STRUCTURES, SYSTEMS, AND METHODS FOR USE IN NANO-ENHANCED RAMAN SPECTROSCOPY (NERS)

FIELD OF THE INVENTION

The present invention relates to Raman spectroscopy. More particularly, the present invention relates to nano-enhanced Raman spectroscopy (NERS), to structures that enhance Raman scattered radiation that is scattered by an analyte (e.g., NERS-active structures), to methods of making such structures, to Raman spectroscopy systems including such structures, and to methods for performing Raman spectroscopy using such structures.

BACKGROUND OF THE INVENTION

Raman spectroscopy is a technique for analyzing molecules or materials. In conventional Raman Spectroscopy, an analyte (or sample) that is to be analyzed is irradiated with high intensity monochromatic electromagnetic radiation provided by a radiation source, such as a laser. An electromagnetic radiation detector detects radiation that is scattered by the analyte. The characteristics of the scattered radiation provide information relating to the analyte.

Conventional Raman spectroscopy systems typically include an electromagnetic radiation source that is configured to emit incident electromagnetic radiation, an analyte stage on which an analyte may be positioned, and an electromagnetic radiation detector. The radiation detector is configured to detect at least a portion of scattered radiation that is scattered by the analyte. Raman spectroscopy systems also typically include various optical components positioned between the radiation source and the analyte stage, and between the analyte stage and the radiation detector. Such optical components may include, for example, lenses, filters, and apertures.

The radiation source may be a commercially available laser. The wavelength or wavelengths of incident electromagnetic radiation that may be emitted by the electromagnetic radiation source typically are within or near the visible region of the electromagnetic radiation spectrum.

The radiation detector receives and detects at least a portion of the scattered radiation that is scattered by an analyte disposed on the analyte stage. The detector includes a device for determining the wavelength of the scattered radiation (for example, a monochromator) and a device for determining the intensity of the scattered radiation (for example, a photomultiplier). Typically, the scattered radiation is scattered in all directions relative to the analyte stage.

Optical components positioned between the radiation source and the analyte stage may be used to collimate, filter, and/or focus the incident radiation before the incident radiation impinges on the analyte stage. Similarly, optical components positioned between the analyte stage and the radiation detector may be used to collimate, filter, and/or focus the scattered radiation.

To perform Raman spectroscopy using a Raman spectroscopy system, an analyte is provided on an analyte stage of a Raman spectroscopy system and irradiated with incident radiation emitted by a radiation source. As the incident radiation impinges on the analyte, at least some of the incident radiation will be scattered by the analyte. A majority of the photons of the incident radiation that impinge on the analyte are elastically scattered by the analyte. In other words, the scattered photons have the same energy, and thus the same wavelength, as the incident photons. This elastic scattering of photons is termed "Rayleigh scattering," and radiation consisting of these elastically scattered photons is termed "Rayleigh-scattered radiation" or "Rayleigh radiation."

The Rayleigh scattering process can be further described with reference to the simplified Jablonski diagram shown schematically in FIG. 1, which illustrates various energy levels of a hypothetical analyte. In FIG. 1, energy levels of the analyte are represented as horizontal lines. As seen therein, the ground state energy level (the lowest energy level) is shown at the bottom of the diagram, excited vibrational energy states are shown just above the ground state, excited electronic energy states are shown at the top of the diagram, and virtual excited states are shown between the excited electronic states and the excited vibrational states. As seen in FIG. 1, Rayleigh scattering typically involves absorption of a single photon of the incident radiation by the analyte, which causes the analyte to transition from the ground state to a virtual state followed by relaxation to the ground state. As the analyte relaxes to the ground state, the analyte emits a photon of scattered radiation that has energy equal to that of the photon of the incident radiation. In this manner, the photon of the incident radiation is considered to have been elastically scattered.

In addition to the Rayleigh scattering of photons, a very small fraction of the photons of the incident radiation may be inelastically scattered by the analyte. Typically, only about 1 in $10^7$ of the photons of the incident radiation is inelastically scattered by the analyte. These inelastically scattered photons have a different wavelength than the photons of the incident radiation. This inelastic scattering of photons is termed "Raman scattering," and radiation consisting of Raman-scattered photons is termed "Raman-scattered radiation" or "Raman radiation." The photons of the Raman-scattered radiation can have wavelengths less than, or more typically, greater than the wavelength of the photons of the incident radiation.

When a photon of the incident radiation collides with the analyte, energy can be transferred from the photon to the analyte or from the analyte to the photon. When energy is transferred form the photon of the incident radiation to the analyte, the Raman-scattered photon will have a lower energy and a corresponding longer wavelength than the incident photon. These Raman-scattered photons having lower energy than the incident photons are collectively referred to in Raman spectroscopy as the "Stokes radiation." As seen in FIG. 1, 1st order Stokes Raman scattering typically involves absorption of a single photon of the incident radiation by the analyte, which causes the analyte to transition from a first energy state (for example, the ground state) to an excited virtual state. The analyte then relaxes to an excited vibrational state of higher energy than the first energy state. As the analyte relaxes to the excited vibrational state, the analyte emits a photon of scattered radiation that has less energy (and a longer wavelength) than the photon of the incident radiation. In this manner, the photon of the incident radiation is considered to have been inelastically scattered.

When energy is transferred from the analyte to a Raman-scattered photon, the Raman-scattered photon will have a higher energy and a corresponding shorter wavelength than the photon of the incident radiation. These Raman-scattered photons, which have higher energy than the incident photons, are collectively referred to in Raman spectroscopy as the "anti-Stokes radiation." As seen in FIG. 1, 1st order anti-Stokes Raman scattering typically involves absorption of a single photon of the incident radiation by the analyte, which causes the analyte to transition from an excited vibrational energy state to an excited virtual state. The analyte then relaxes to a lower energy state (for example, the ground state) than the excited vibrational energy state. As the analyte relaxes to the lower energy state, the analyte emits a photon of scattered radiation that has more energy (and a shorter wavelength) than the photon of the incident radiation. In this manner, the photon of the incident radiation is considered to have been inelastically scattered.

The shift in energy (wavelength, frequency, or wave number) of the Raman-scattered photons in relation to the Rayleigh scattered photons is known as the "Raman shift."

Raman scattering primarily involves a one photon excitation—one photon relaxation process. These Raman scattering processes are often referred to as "1st order" Raman scattering processes. However, multiple photon excitation single photon relaxation processes are also observed and are referred to as "hyper Raman scattering" processes. Two photon excitation—one photon relaxation scattering processes are referred to as "2nd order" hyper Raman scattering processes, three-photon excitation—one photon relaxation processes are referred to as "3rd order" Raman scattering processes, etc. These higher order Raman scattering processes are often referred to as "harmonics."

In 2nd order scattering processes, a molecule of the analyte in an initial energy state absorbs the energy from two photons of the incident radiation causing an energy transition in the analyte to a virtual excited state, followed by relaxation to a final energy state and emission of a single scattered photon. If the final energy state is the same as the initial energy state, the scattering process is referred to as hyper Raleigh scattering. If the final energy state is higher than the initial energy state, the scattering process is referred to as 2nd order Stokes hyper Raman scattering. Finally, if the final energy state is lower than the initial energy state, the scattering process is referred to as 2nd order anti-Stokes hyper Raman scattering. The Stokes and anti-Stokes 2nd order hyper Raman scattering processes are also represented in the Jablonski diagram shown in FIG. 1.

Information may be obtained from hyper Raman-scattered radiation that cannot be obtained from 1st order Raman-scattered radiation. In particular, vibrational information may be suppressed in Raman-scattered radiation due to symmetry issues, thereby resulting in what are often referred to as "silent modes." These silent modes may not be suppressed in the hyper Raman-scattered radiation.

When an analyte is irradiated with incident radiation, the scattered radiation may include Raman-scattered radiation, which may comprise 1st order Raman-scattered radiation (Stokes and anti-Stokes) and higher order hyper Raman-scattered radiation (Stokes and anti-Stokes), in addition to Rayleigh scattered radiation. The Raman-scattered radiation that is scattered by the analyte (including the hyper Raman-scattered radiation) is often referred to as the "Raman signal."

The Raman signal is detected using the radiation detector. The wavelengths and corresponding intensity of the Raman-scattered radiation may be determined and used to provide a Raman spectral graph. Analytes generate unique Raman spectral graphs. The unique Raman spectral graph obtained by performing Raman spectroscopy can be used to obtain information relating to the analyte including, but not limited to, the identification of an unknown analyte, or the determination of physical and chemical characteristics of a known analyte.

The number of Raman-scattered photons that are scattered by an analyte is extremely small relative to the number of Rayleigh scattered photons, and the number of hyper Raman-scattered photons is even smaller than the number of 1st order Raman-scattered photons. Typical radiation detectors are capable of detecting the high-intensity Rayleigh scattered radiation in addition to the low-intensity Raman-scattered radiation. The detection of the Raman-scattered radiation may be difficult due to the high intensity of the Rayleigh scattered radiation. To overcome this difficulty, a radiation filter may be positioned between the analyte stage and the detector to prevent the Rayleigh scattered radiation from being detected by the detector, thus allowing only the Raman-scattered radiation to be received by the detector. Commercially available notch filters may be used for such purposes.

After removal of the Rayleigh scattered radiation, the various wavelengths of Raman-scattered radiation typically are spatially separated using a diffraction grating. The separated wavelengths of Raman-scattered radiation typically are detected or imaged simultaneously using a charge coupled device (CCD) array. Alternatively, the wavelengths of Raman-scattered radiation may be detected using a photomultiplier tube (PMT).

Surface-enhanced Raman spectroscopy (SERS) is a technique that allows for enhancement of the intensity of the Raman-scattered radiation relative to conventional Raman spectroscopy (i.e., the number of Raman-scattered photons that are scattered by an analyte). In SERS, the analyte typically is adsorbed onto or placed adjacent to what is often referred to as a SERS-active structure. SERS-active structures typically include a metal surface or structure. Interactions between the analyte and the metal surface may cause an increase in the intensity of the Raman-scattered radiation.

Several types of metallic structures have been employed in SERS techniques to enhance the intensity of Raman-scattered radiation that is scattered by an analyte. Some examples of such structures include electrodes in electrolytic cells, metal colloid solutions, and metal substrates such as a roughened metal surface or metal "islands" formed on a substrate. For example, it has been shown that adsorbing analyte molecules onto or near a specially roughened metal surface of gold or silver can enhance the Raman scattering intensity by factors of between $10^3$ and $10^6$.

Raman spectroscopy recently has been performed employing metal nanoparticles, such as nanometer scale needles, particles, and wires, as opposed to a simple roughened metallic surface. This process will be referred to herein as nano-enhanced Raman spectroscopy (NERS). Structures comprising nanoparticles or other nano-scale structures that are used to enhance the intensity of Raman-scattered radiation may be referred to as NERS-active structures. The intensity of the Raman-scattered radiation that is scattered by an analyte adsorbed on such a NERS-active structure can be increased by factors as high as $10^{16}$.

BRIEF SUMMARY OF THE INVENTION

In one aspect, the present invention includes a NERS-active structure that includes a plurality of protrusions extending from a surface of a substrate. The plurality of protrusions includes a first protrusion and a second protrusion. Raman signal-enhancing material is disposed on at least one surface of the first protrusion and projects laterally in a direction generally towards the second protrusion. Similarly, Raman signal-enhancing material is disposed on at least one surface of the second protrusion and projects laterally in a direction generally towards the first protrusion.

In some embodiments, at least a portion of the Raman signal-enhancing material projecting from the first protrusion and at least a portion of the Raman signal-enhancing material projecting from the second protrusion may be separated by a distance of less than about ten nanometers.

In another aspect, the present invention includes a method of forming a NERS-active structure. A substrate is provided having a plurality of protrusions extending from a surface of the substrate. Raman signal-enhancing material is applied to at least one surface of a first protrusion so that it projects in a lateral direction relative to the surface of the substrate generally towards a second protrusion. Similarly, Raman signal-enhancing material is applied to at least one surface of the second protrusion so that it projects in a lateral direction relative to the surface of the substrate generally towards the first protrusion. At least a portion of the Raman signal-enhancing material on the first protrusion may be caused to be separated from at least a portion of the Raman signal-enhancing material on the second protrusion by a distance of less than about 10 nanometers.

In another aspect, the present invention includes a Raman spectroscopy system that includes a radiation source, a NERS-active structure, and a detector configured to detect Raman scattered radiation. The NERS-active structure includes a plurality of protrusions extending from a surface of a substrate. The plurality of protrusions includes a first protrusion and a second protrusion. Raman signal-enhancing material is disposed on at least one surface of the first protrusion and projects laterally in a direction generally towards the second protrusion. Similarly, Raman signal-enhancing material is disposed on at least one surface of the second protrusion and projects laterally in a direction generally towards the first protrusion. In some embodiments, at least a portion of the Raman signal-enhancing material projecting from the first protrusion and at least a portion of the Raman signal-enhancing material projecting from the second protrusion may be separated by a distance of less than about ten nanometers.

In yet another aspect, the present invention includes a method of performing Raman spectroscopy on an analyte. A NERS-active structure is provided that includes a plurality of protrusions extending from a surface of a substrate. The plurality of protrusions includes a first protrusion and a second protrusion. Raman signal-enhancing material is disposed on at least one surface of the first protrusion and projects laterally in a direction generally towards the second protrusion. Similarly, Raman signal-enhancing material is disposed on at least one surface of the second protrusion and projects laterally in a direction generally towards the first protrusion. In some embodiments, at least a portion of the Raman signal-enhancing material projecting from the first protrusion and at least a portion of the Raman signal-enhancing material projecting from the second protrusion may be separated by a distance of less than about ten nanometers. An analyte is provided proximate the NERS-active structure and irradiated with electromagnetic radiation. Raman scattered radiation that is scattered by the analyte is detected.

The features, advantages, and alternative aspects of the present invention will be apparent to those skilled in the art from a consideration of the following detailed description taken in combination with the accompanying drawings.

BRIEF DESCRIPTION OF THE SEVERAL VIEWS OF THE DRAWINGS

While the specification concludes with claims particularly pointing out and distinctly claiming that which is regarded as the present invention, the advantages of this invention can be more readily ascertained from the following description of the invention when read in conjunction with the accompanying drawing in which:

DETAILED DESCRIPTION OF THE INVENTION

The term "analyte" as used herein means any molecule, molecules, material, substance, or matter that is to be analyzed or detected by Raman spectroscopy.

The term "nanoparticle" as used herein means a particle of any shape having cross-sectional dimensions of less than about 100 nanometers. Examples of nanoparticles include, but are not limited to, nanodots (including quantum dots), nanowires, nanolines, nanocolumns, and nanospheres.

The term "Raman signal-enhancing material" as used herein means a material that, when formed into appropriate geometries or configurations, is capable of increasing the number of Raman scattered photons that are scattered by an analyte when the analyte is located proximate to that material, and when the analyte and material are subjected to electromagnetic radiation. Raman signal-enhancing materials include, but are not limited to, silver, gold, and copper. Raman signal-enhancing materials are used to form Raman signal-enhancing structures.

The term "Raman signal-enhancing structure" as used herein means a structure that is capable of increasing the number of Raman scattered photons that are scattered by an analyte when the analyte is located proximate to the structure, and the analyte and structure are subjected to electromagnetic radiation.

The term "NERS-active structure" as used herein means a Raman signal-enhancing structure employing nanoparticles to increase the number of Raman scattered photons that are scattered by an analyte when the analyte is located proximate to the structure.

The illustrations presented herein are not meant to be actual views of any particular Raman-enhancing structure or Raman spectroscopy system, but are merely idealized representations which are employed to describe the present invention. Additionally, elements common between figures may retain the same numerical designation.

Figure 2:
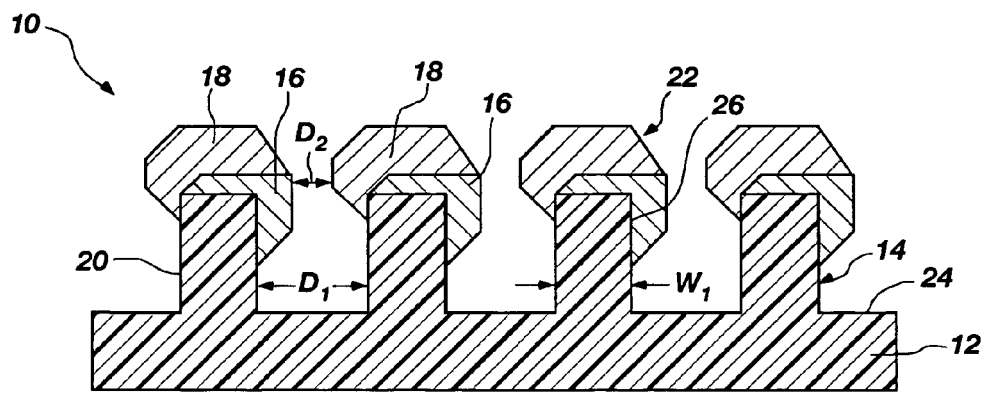
FIG. 2 is an idealized cross section view of one example of a NERS-active structure that embodies teachings of the present invention.
Figure 3:
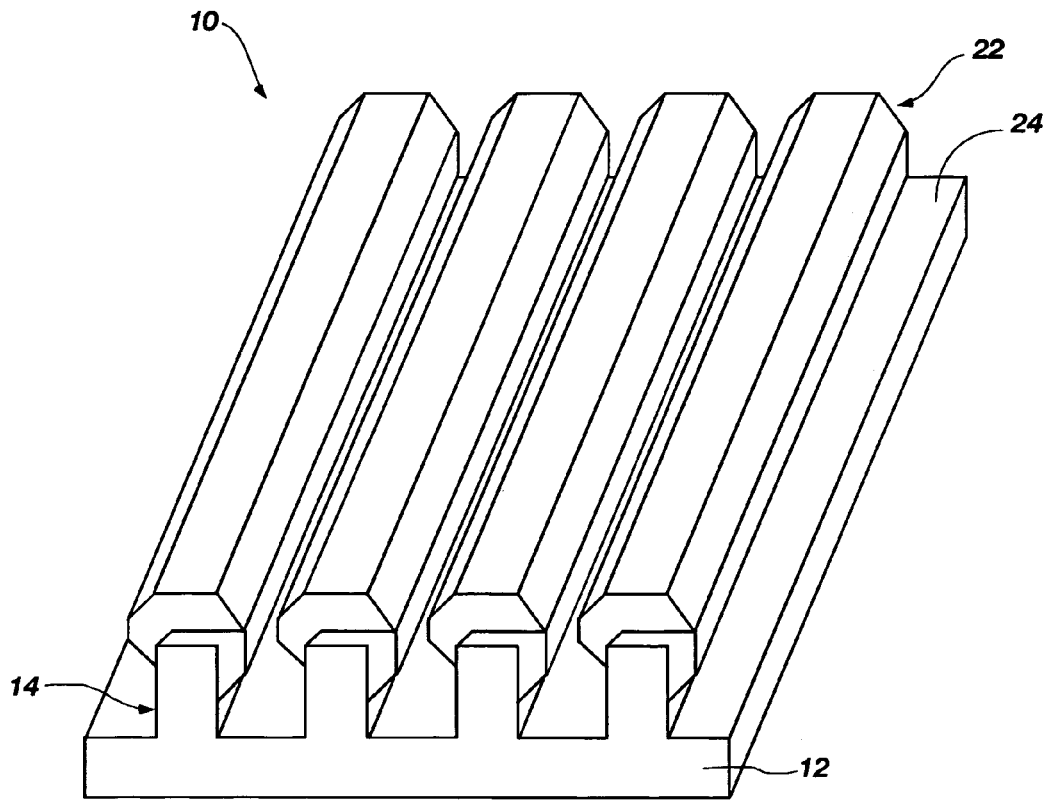
FIG. 3 is a perspective view of the NERS-active structure shown in FIG. 2.

One example of a NERS-active structure 10 that embodies teachings of the present invention is shown in FIGS. 2 and 3. The NERS-active structure 10 may include a substrate 12 and a plurality of protrusions 14 that each extend from a surface 24 of the substrate 12. In some embodiments of the present invention, the plurality of protrusions 14 may be discrete structures from the substrate 12 or they may be integrally formed as part of the substrate, as shown in FIG. 2. The surface 24 of the substrate 12 may be substantially planar.

In some embodiments, the plurality of protrusions 14 may be disposed in a periodic array on the surface 24 of the substrate 12. By way of example and not limitation, each of the protrusions 14 may be or may include a nanoline that extends along the surface 24 of the substrate 12. In some embodiments, the nanolines may extend substantially parallel to one another (as shown in FIG. 3), and may be separated from one another. By way of example and not limitation, in some embodiments, each protrusion 14 may be a nanoline having a rectangular cross-sectional shape having and a width $W_1$ of approximately 50 nanometers or less. In other embodiments the width $W_1$ may be several millimeters. In some embodiments, the shortest distance $D_1$ between at least two of the protrusions 14 may be less than about 20 nanometers.

Raman signal-enhancing material 22 may be disposed on at least one surface 26 of the protrusions 14. At least a portion of the Raman signal-enhancing material 22 disposed on each of the protrusions 14 may project in a lateral direction generally towards an adjacent protrusion 14, as shown in FIG. 2. In some embodiments of the present invention, the Raman signal-enhancing material 22 that is disposed on each of the protrusions 14 may include one or more grains 16 of Raman signal-enhancing material that project in a lateral direction generally towards an adjacent protrusion 14 on one side of the protrusion 14 on which the Raman signal-enhancing material is disposed, and one or more grains 18 or Raman signal-enhancing material that project in a lateral direction generally towards another adjacent protrusions 14 on an opposite side of the protrusion 14 on which the Raman signal-enhancing material is disposed. By way of example, the shortest distance $D_2$ between the Raman signal-enhancing material 22 on adjacent protrusions 14 may be less than about 5 nanometers.

The Raman signal enhancing material 22 may be a metal such as, for example, gold, silver, or copper. The substrate 12 may include a generally planar layer of metal, semiconductor, dielectric, ceramic, or a polymer material.

Additionally, each protrusion of the plurality of protrusions 14 may have a portion 20 that is not covered by any Raman signal-enhancing material 22. As illustrated in FIG. 2, the portion 20 without any Raman signal-enhancing material 22 thereon may be located proximate the surface 24 of the substrate 12. Furthermore, in some embodiments, the substrate 12 may not have any Raman signal-enhancing material 22 deposited on its surface 24, as shown in FIG. 2.

The NERS-active structure 10 may be used to perform Raman spectroscopy on an analyte, and may be used to enhance the Raman signal emitted by the analyte. For example, an analyte (not shown) may be positioned adjacent the NERS-active structure 10, and in particular, proximate the distance $D_2$ between the Raman signal-enhancing material 22 disposed on adjacent protrusions 14. The analyte and the NERS-active structure 10 then may be irradiated with incident electromagnetic radiation, and the Raman-scattered radiation that is scattered by the analyte may be detected using a detector.

While the NERS-active structure 10 shown in FIGS. 2-3 includes Raman signal-enhancing material 22 disposed on protrusions 14 that each include elongated, substantially parallel nanolines extending along the surface of a substrate, the present invention is not so limited, and the NERS-active structures that embody teachings of the present invention may include protrusions having other shapes and configurations.

Figure 4:
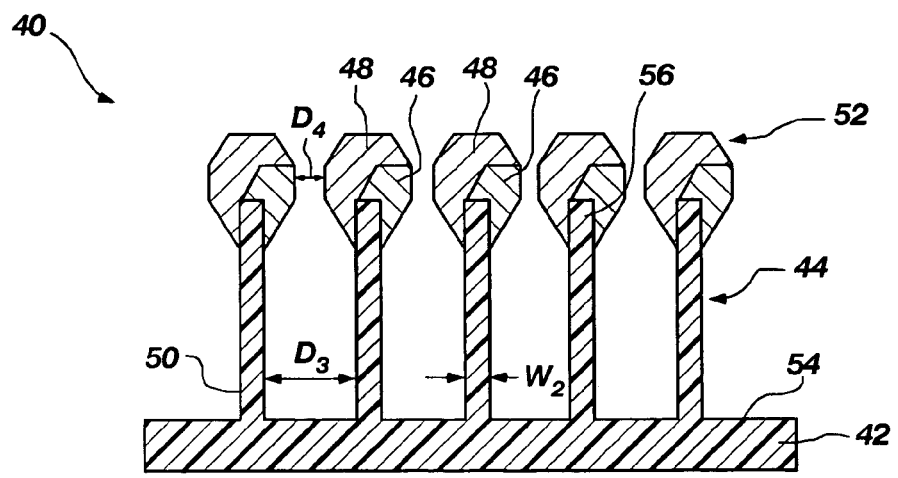
FIG. 4 is a cross section view of another example of a NERS-active structure that embodies teachings of the present invention.
Figure 5:
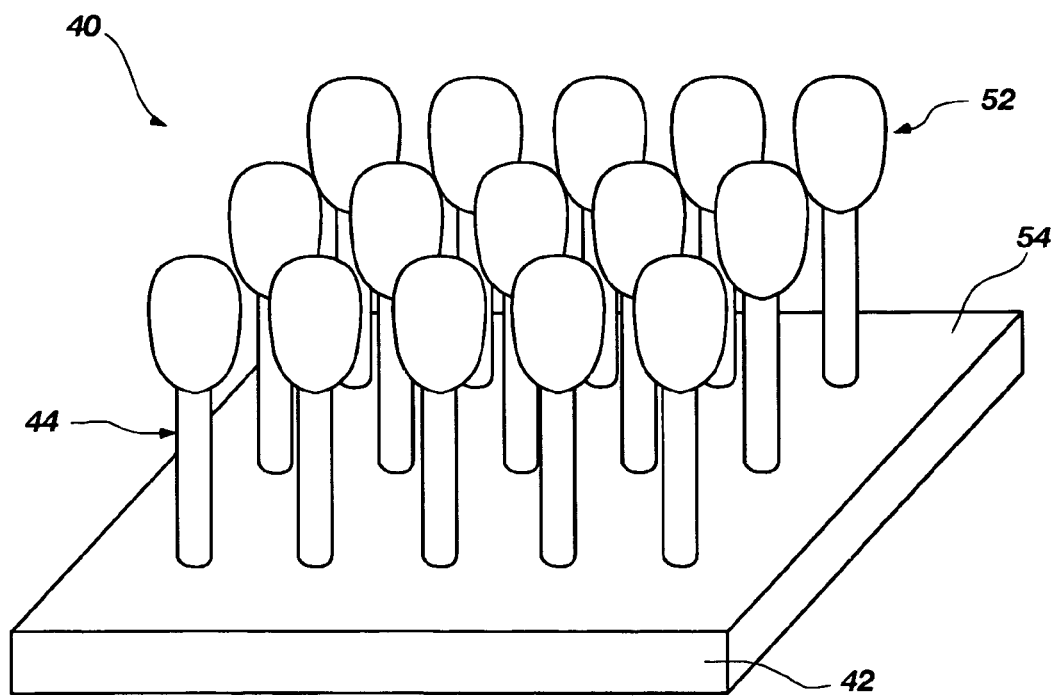
FIG. 5 is a perspective view of the NERS-active structure shown in FIG. 4.

Another example of a NERS-active structure 40 that embodies teachings of the present invention is shown in FIGS. 4 and 5. The NERS-active structure 40 may include a substrate 42 and a plurality of protrusions 44 that each extend from a surface 54 of the substrate 42. The surface 54 of the substrate 42 may be substantially planar.

In some embodiments, the plurality of protrusions 44 may be disposed in a periodic array on the surface 54 of the substrate 42. By way of example and not limitation, each of the protrusions 44 may be or may include a nanocolumn that extends from the surface 54 of the substrate 42. In some embodiments, the nanocolumns may extend substantially parallel to one another (as shown in FIG. 5), and may be substantially uniformly separated from one another. For example, each protrusion 44 may be a nanocolumn having a circular cross-sectional shape having and a diameter or width $W_2$ of approximately 50 nanometers or less. In other embodiments, the diameter or width $W_2$ may be several millimeters. Furthermore, the shortest distance $D_3$ between at least two adjacent protrusions 54 may be less than about 20 nanometers.

Raman signal-enhancing material 52 may be disposed on at least one surface 56 of the protrusions 44. At least a portion of the Raman signal-enhancing material 52 disposed on each of the protrusions 44 may project in a lateral direction extending from the protrusion 44 (on which the Raman signal-enhancing material 52 disposed) generally towards an adjacent protrusion 44, as shown in FIG. 4.

In some embodiments, the Raman signal-enhancing material 52 that is disposed on each of the protrusions 44 may include one or more grains 46 of Raman signal-enhancing material that project in a lateral direction generally towards an adjacent protrusion 44 on one side of the protrusion 44 on which the Raman signal-enhancing material is disposed, and one or more grains 48 or Raman signal-enhancing material that project in a lateral direction generally towards another adjacent protrusion 44 on an opposite side of the protrusion 44 on which the Raman signal-enhancing material is disposed. For example, the shortest distance $D_4$ between the Raman signal-enhancing material 52 on adjacent protrusions 44 may be less than about 5 nanometers.

The Raman signal enhancing material 52 may be or include a metal such as, for example, gold, silver, copper, or an alloy based on at least one of such metals. The substrate 42 may include a generally planar layer of metal, ceramic, or a polymer material.

Additionally, each protrusion of the plurality of protrusions 44 may have a portion 50 that is not covered by any Raman signal-enhancing material 52. As illustrated in FIG. 4, the portion 50 without any Raman signal-enhancing material 52 thereon may be located proximate the surface 54 of the substrate 42. Furthermore, in some embodiments, the substrate 42 may not have any Raman signal-enhancing material 52 deposited on its surface 54, as shown in FIG. 5.

The NERS-active structure 40 may be used to perform Raman spectroscopy on an analyte and may be used to enhance the Raman signal emitted by the analyte. For example, an analyte (not shown) may be positioned adjacent the NERS-active structure 40 and between the Raman signal-enhancing material 52 disposed on adjacent protrusions 44. The analyte and the NERS-active structure 40 then may be irradiated with incident electromagnetic radiation, and the Raman-scattered radiation that is scattered by the analyte may be detected using a detector.

While the NERS-active structures 10 shown in FIGS. 2-3 and the NERS-active structure 40 shown in FIGS. 4-5 each include Raman signal-enhancing material 22, 52 disposed on the upper portion of each of the protrusions 14, 44 and no Raman signal-enhancing material on the substrate 12, 42, the present invention is not so limited, and NERS-active structures that embody teachings of the present invention may include Raman signal-enhancing material disposed on the protrusions in other configurations.

Figure 6:
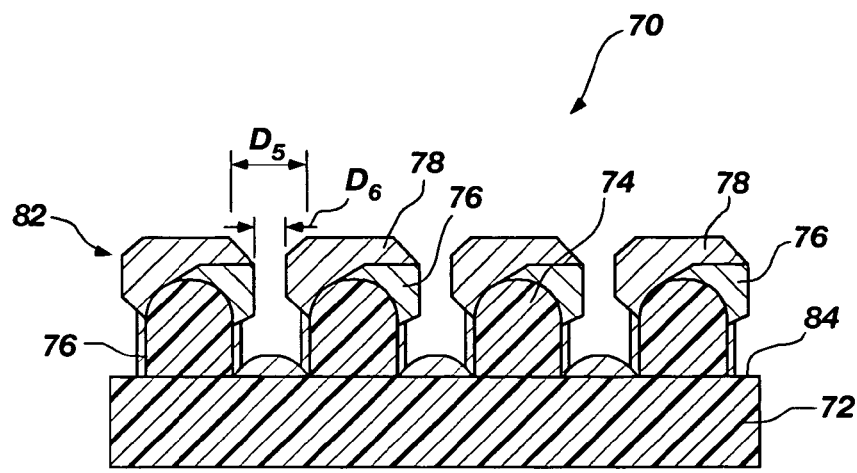
FIG. 6 is a cross section view of yet another example of a NERS-active structure that embodies teachings of the present invention.
Figure 7:
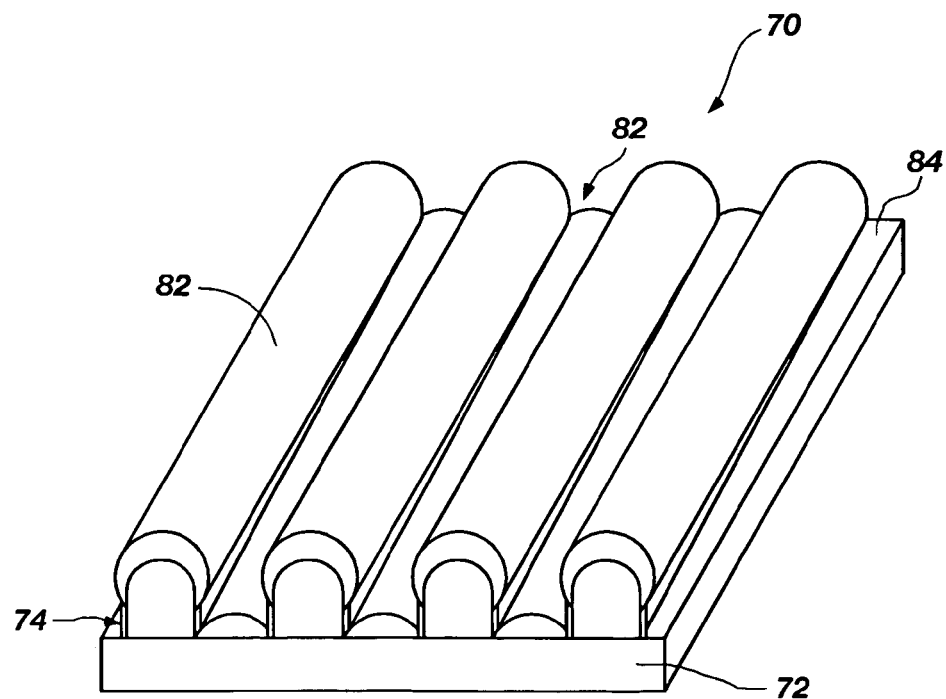
FIG. 7 is a perspective view of the NERS-active structure shown in FIG. 6.

Yet another example of a NERS-active structure 70 that embodies teachings of the present invention is shown in FIGS. 6 and 7. The NERS-active structure 70 may include a substrate 72 and a plurality of protrusions 74 that each extend from a surface 84 of the substrate 72. The surface 84 of the substrate 72 may be substantially planar.

In some embodiments, the plurality of protrusions 74 may be disposed in a periodic array on the surface 84 of the substrate 72. By way of example and not limitation, each of the protrusions 74 may be or may include a nanoline that extends from the surface 84 of the substrate 72. In some embodiments, the nanolines may extend substantially parallel to one another (as shown in FIG. 7), and may be separated from one another. By way of example and not limitation, in some embodiments, each protrusion 74 may be a nanoline having a generally rounded cross-sectional shape and a width of less than about 50 nanometers. In other embodiments the width $W_3$ may be as large as several millimeters. In some embodiments, the shortest distance $D_5$ between at least two adjacent protrusions 74 may be less than about 20 nanometers.

Raman signal-enhancing material 82 may be disposed on at least one surface of the protrusions 74. At least a portion of the Raman signal-enhancing material 82 disposed on each of the protrusions 74 may project in a lateral direction generally towards an adjacent protrusion 74, as shown in FIG. 6. In some embodiments of the present invention, the Raman signal-enhancing material 82 that is disposed on each of the protrusions 74 may include one or more grains 76 of Raman signal-enhancing material 82 that project in a lateral direction generally towards an adjacent protrusion 74 on one side of the protrusion 74 on which the Raman signal-enhancing material 82 is disposed, and one or more grains 78 of Raman signal-enhancing material 82 that project in a lateral direction generally towards another adjacent protrusion 74 on an opposite side of the protrusion 74 on which the Raman signal-enhancing material 82 is disposed. For example, the shortest distance $D_6$ between the Raman signal-enhancing material 82 on adjacent protrusions 74 may be less than about 5 nanometers.

The Raman signal enhancing material 82 may be or may include a metal such as, for example, gold, silver, copper, or an alloy based on at least one of such metals. The substrate 72 may include a generally planar layer of metal, ceramic, or a polymer material.

Additionally, each of the protrusions 74 and the surface 84 of the substrate 72 from which the protrusions 74 project may be substantially covered by the Raman signal-enhancing material 82, as illustrated in FIGS. 6-7.

The NERS-active structure 70 may be used to perform Raman spectroscopy on an analyte, and may be used to enhance the Raman signal emitted by the analyte. For example, an analyte (not shown) may be positioned adjacent the NERS-active structure 70 and, in particular, between the Raman signal-enhancing material 82 disposed on adjacent protrusions 74. The analyte and the NERS-active structure 70 then may be irradiated with incident electromagnetic radiation, and the Raman-scattered radiation that is scattered by the analyte may be detected using a detector.

Figure 1:
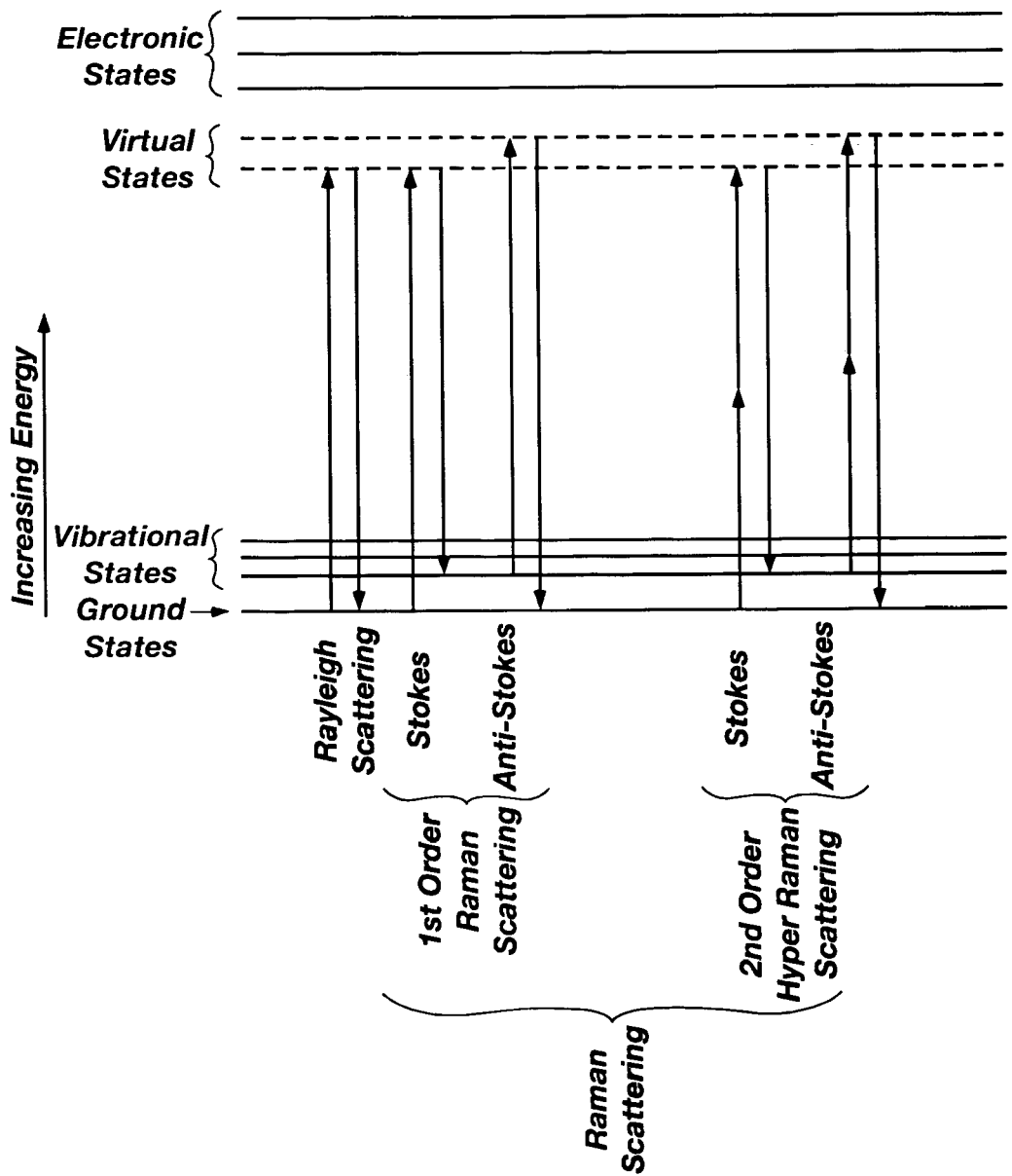
FIG. 1 is a Jablonski energy level diagram schematically representing Rayleigh and Raman scattering processes for a hypothetical analyte.

Various embodiments of the present invention also include methods of forming NERS-active structures, such as those previously described herein. One example of a method that embodies teachings of the present invention and that may be used to form a NERS-active structure that embodies teachings of the present invention, such as, for example, the NERS-active structure 10 shown in FIGS. 1-2, is described below with reference to FIGS. 8, 9A-9G, and FIGS. 10A-10C.

Figure 8:
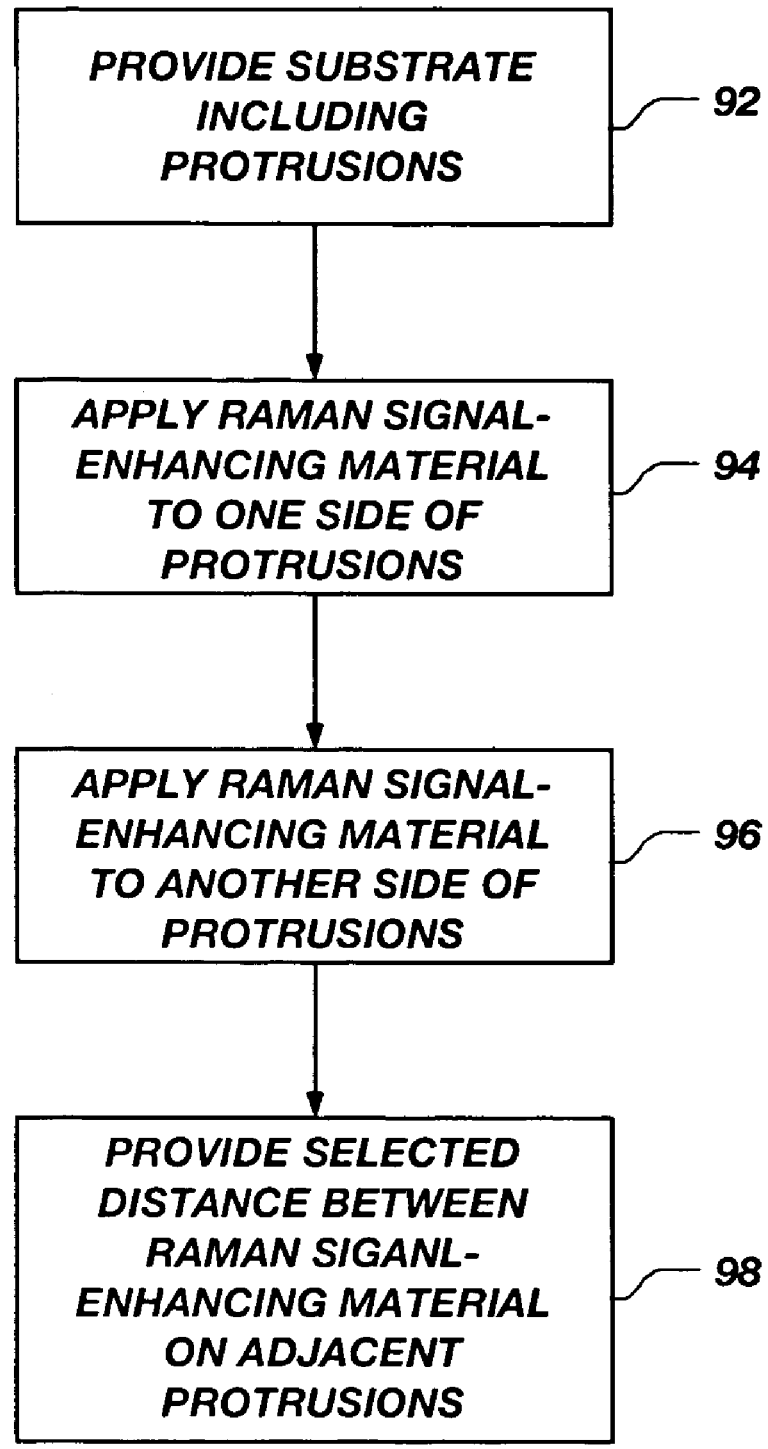
FIG. 8 is a flowchart showing various steps in one example of a method for forming a NERS-active structure that embodies teachings of the present invention.

FIG. 8 is a flow chart broadly illustrating methods that embody teachings of the present invention. Referring to FIG. 8, a substrate may be provided that includes a plurality of protrusions or other features that protrude or extend from at least one surface of the substrate, 92. Various methods may be used to provide such a substrate including, for example, photolithography, imprint lithography (including nanoimprint lithography), electron beam lithography, laser machining, etc. One example of a nanoimprint lithography method that may be used to provide a substrate that includes a plurality of protrusions or other features is described below with reference to FIGS. 9A-9E.

Figure 9A:
FIGS. 9A-9G illustrate one example of a method that embodies teachings of the present invention and that may be used to form NERS-active structures that also embody teachings of the present invention.

Referring to FIG. 9A, a substrate 12 may be provided. The substrate 12 may be or include a substantially planar layer of metal, semiconductor, dielectric, ceramic, or a polymer material. By way of example and not limitation, the substrate 12 may include a silicon substrate, a glass substrate, or a sapphire substrate.

Figure 9B:
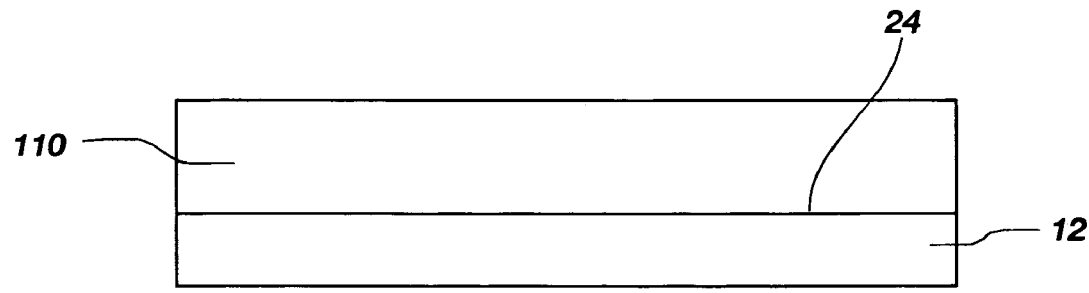

As shown in FIG. 9B, a layer of deformable material 110 may be applied to a surface 24 of the substrate 12. The layer of deformable material 110 may include, for example, a layer of polymethylmethacrylate (PMMA) or any other commercially available nanoimprint resist. Furthermore, the layer of deformable material 110 may solidify upon application of energy (such as radiation or heat) to the layer of deformable material 110. Such nanoimprint lithography resists are sold by, for example, Nanonex of Monmouth Junction, N.J.

Figure 9C:
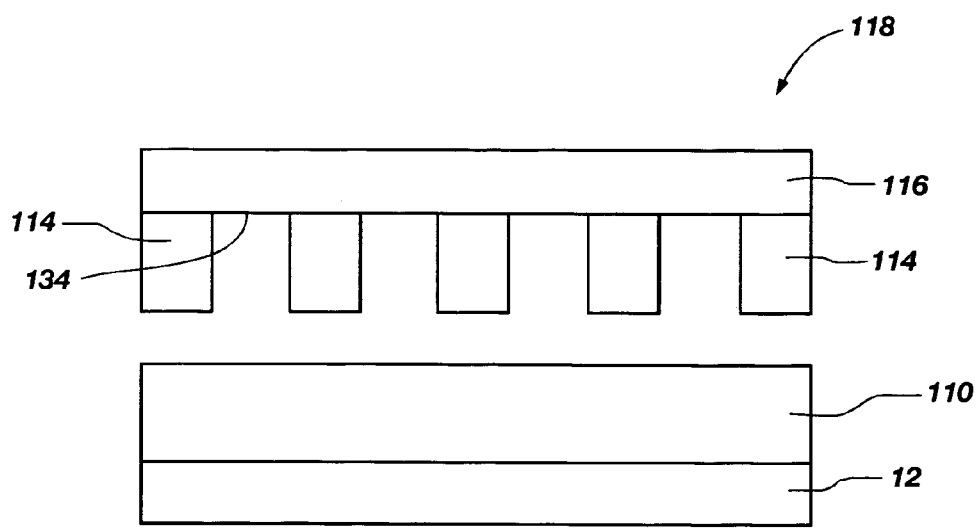

Referring to FIG. 9C, a nanoimprint mold 118 may be provided with a mold base 116 and a plurality of protrusions 114 formed on or in a surface 134 of the mold base 116. By way of example and not limitation, the mold base 116 may comprise silica, gallium arsenide, silicon, or any other suitable metal, ceramic, or polymer material.

Figure 9D:
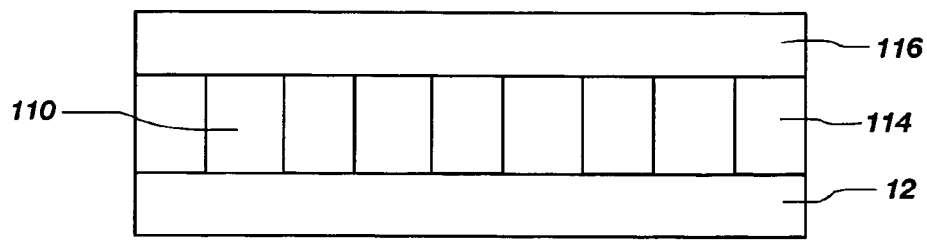
Figure 9E:
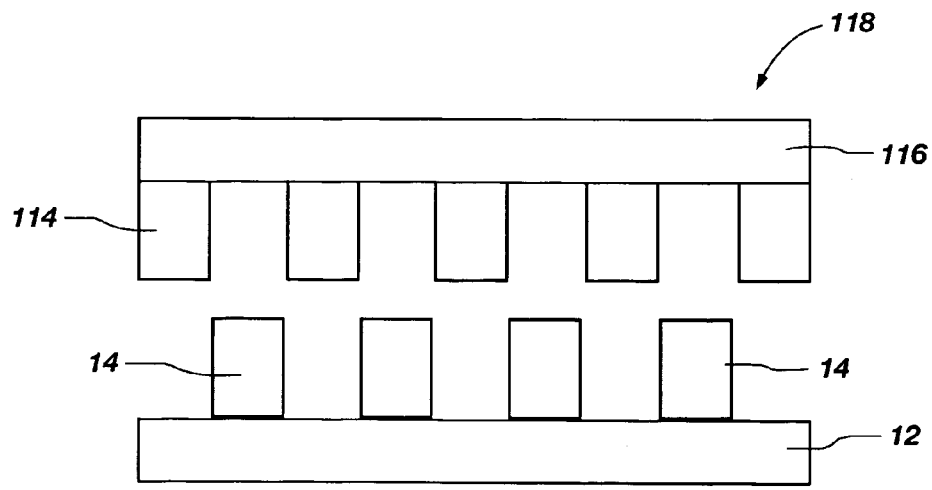

As shown in FIG. 9D, the plurality of protrusions 114 of the nanoimprint mold 118 may be pressed into the layer of deformable material 110 to form corresponding protrusions and gaps in the layer of deformable material 110. The layer of deformable material 110 may be at least partially cured to solidify the plurality of protrusions 14, and the nanoimprint mold 118 may be separated from the substrate 12 and the cured layer of deformable material 110, as shown in FIG. 9E. In this manner, a plurality of protrusions 14 may be formed in the layer of deformable material 110 by the nanoimprint mold 118. In this embodiment, the protrusions 14 extending from the surface of the substrate 12 may comprise discrete structures formed on the surface of the substrate 12 from the layer of deformable material 110 (e.g., polymethylmethacrylate).

In additional embodiments, the protrusion 14 may be integrally formed with the substrate 12. For example, in some methods, after the plurality of protrusions 14 are formed in the layer of deformable material 110 on the surface of the substrate 12, integral protrusions may be formed in the substrate 12 by etching (e.g., wet etching or dry etching) the exposed regions of the surface of the substrate 12 between the protrusions 14 formed in the layer of deformable material 110, and subsequently removing the protrusions formed in the deformable material 110 from the surface of the substrate 12.

The nanoimprint method described above is set forth merely as one example of a method that may be used to provide a substrate that includes a plurality of protrusions or other features that protrude or extend from at least one surface of the substrate. It is contemplated that various other methods, including those previously mentioned herein, also may be used to provide such a substrate.

Referring again to FIG. 8, after providing a substrate that includes a plurality of protrusions or other features, Raman signal-enhancing material may be applied to one side of each of at least two of the protrusions, 94.

Figure 9F:
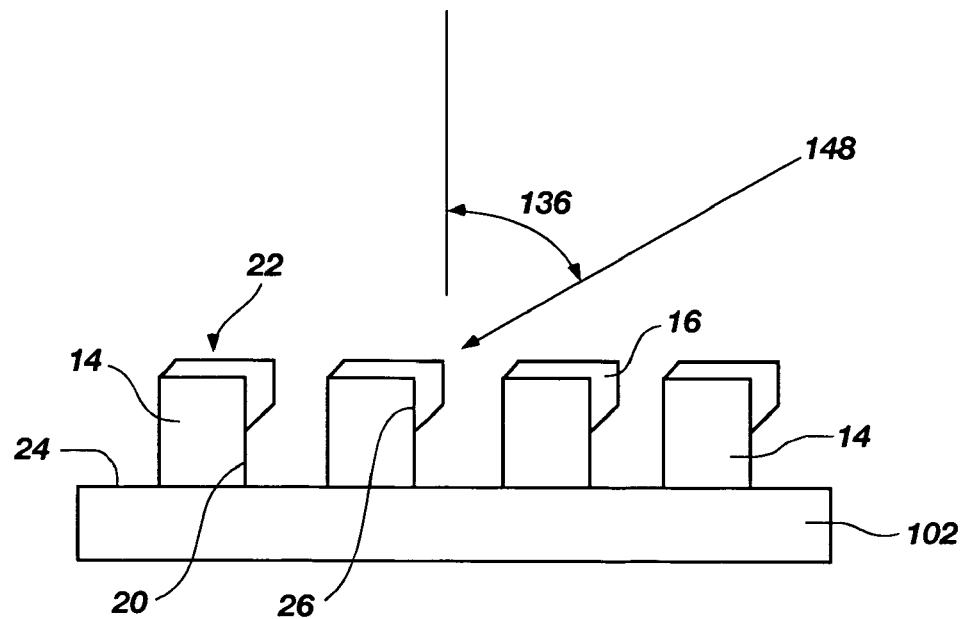

Referring to FIG. 9F, Raman signal-enhancing material 22 may be applied to surfaces 26 of each of the protrusions 14 using shadow deposition techniques.

More specifically, the Raman signal-enhancing material 22 may be applied to at least one surface 26 of each of the protrusions 14 by establishing a flow of atoms or particles of Raman signal-enhancing material 22 in a direction 148, and orienting the surface 26 of each of the protrusions 14 at an acute angle 136 relative to the direction 148 such that the atoms or particles of Raman signal-enhancing material 22 impinge on at least a portion of the surfaces 26 of the protrusions 14. The flow of atoms or particles of Raman signal-enhancing material 22 may be established by, for example, using a conventional deposition process such as, for example, a physical deposition process (e.g., thermal evaporation, electron beam evaporation, sputtering, etc.), a chemical deposition process (e.g., electroless deposition, chemical vapor deposition, etc.), or an atomic layer deposition process.

In addition, the Raman signal-enhancing material 22 may be deposited on the protrusions 14 using a shadow deposition technique. For example, the substrate 12 and the protrusions 14 thereon may be further oriented such that at least some of the protrusions 14 shield at least a portion 20 of an adjacent protrusion 14 from the flow of atoms or particles of Raman signal-enhancing material 22. In other words, at least a portion of at least some of the protrusions 14 may be disposed in a shadow relative to the flow of atoms or particles of Raman signal-enhancing material 22 that is cast by an adjacent protrusion 14.

Shielding the portions 20 of the protrusions 14 may hinder or prevent a significant quantity of Raman signal-enhancing material 22 from being deposited on the portions 20 of the protrusions 14 proximate the substrate 12.

In some embodiments, as the Raman signal-enhancing material 22 is deposited on at least a portion of the surfaces 26 of the protrusions 14, grains 16 of Raman signal-enhancing material 22 may grow or form that each project in a lateral direction generally towards an adjacent protrusion 14.

Referring again to FIG. 8, after applying Raman signal-enhancing material to one side of the protrusions, Raman signal-enhancing material may be applied to another side of the protrusions, 96.

Figure 9G:
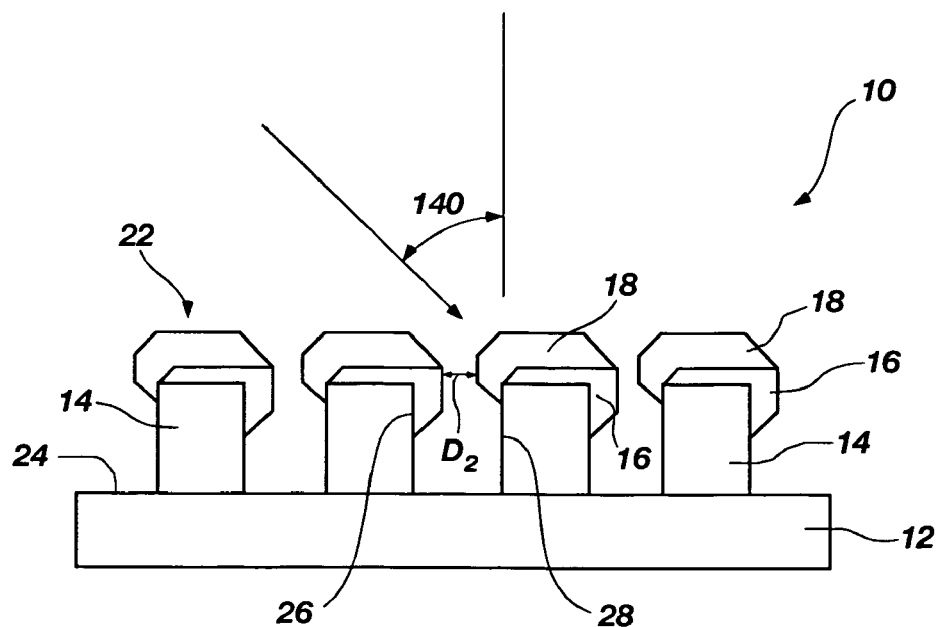

For example, referring to FIG. 9G, Raman signal-enhancing material 22 may be applied to another surface 28 of the protrusions 14 in a manner substantially similar to that described above. The Raman signal-enhancing material 22 may be applied to the additional surface 28 of each of the protrusions 14 by establishing a flow of atoms or particles of Raman signal-enhancing material 22 in a direction 148, and orienting the surface 28 of each of the protrusions 14 at an acute angle 140 relative to the direction 148 such that the atoms or particles of Raman signal-enhancing material 22 impinge on at least a portion of the surfaces 28 of the protrusions 14. In addition, the Raman signal-enhancing material 22 may be deposited on the surfaces 28 of the protrusions 14 using a shadow deposition technique, as described above.

In some embodiments of the present invention, the angle 140 shown in FIG. 9G may be substantially identical in magnitude to the angle 136 shown in FIG. 9F. In additional embodiments, the angle 140 shown in FIG. 9G may have a magnitude that differs from the magnitude of the angle 136 shown in FIG. 9F.

Although not shown in FIGS. 9F-9G, it is contemplated that at least a portion of the surface 24 of the substrate 12 may be covered in Raman-signal enhancing material 22. Furthermore, in additional embodiments, each protrusion 14 may be substantially completely covered by Raman signal-enhancing material 22.

In some embodiments, as the Raman signal-enhancing material 22 is deposited on at least a portion of the surfaces 28 of the protrusions 14, grains 18 of Raman signal-enhancing material 22 may grow or form that each project in a lateral direction generally towards an adjacent protrusion 14 or the grains 16 of Raman signal-enhancing material 22 formed on an adjacent protrusion 14.

Referring yet again to FIG. 8, a selected distance may be provided between the Raman signal-enhancing materials on adjacent protrusions, 98. Referring to FIGS. 9F-9G, in some embodiments of the present invention, the selected distance may be provided by depositing the Raman signal-enhancing material 22 on the surfaces 26 (as shown in FIG. 9F) at a known deposition rate for a selected amount of time, and then depositing the Raman signal-enhancing material 22 on the surfaces 28 (as shown in FIG. 9G) at a known deposition rate for a selected amount of time.

In additional methods, the shadow deposition processes described above with reference to FIGS. 9F-9G may be repeated (i.e., repeatedly and consecutively depositing Raman signal-enhancing material 22 on the surfaces 26 and the surfaces 28 of the protrusions 14) until a selected minimum or average distance $D_2$ is attained between the Raman signal-enhancing material 22 on adjacent protrusions 14.

By way of example and not limitation, in a first step, Raman signal-enhancing material 22 may be deposited on the surfaces 26 of the protrusions 14 (in a manner substantially identical to that previously described in relation to FIG. 9F) until the Raman signal-enhancing material 22 projects in a lateral direction from each of the protrusions 14 by about 3 nanometers in a general direction towards an adjacent protrusion 14. In a second step, Raman signal-enhancing material 22 may be deposited on the surfaces 28 of the protrusions 14 (in a manner substantially similar to that previously described in relation to FIG. 9G) until the Raman signal-enhancing material 22 projects in a lateral direction from each of the protrusions 14 by about 3 nanometers in a direction generally towards an adjacent protrusion 14. The first and second steps then may be repeated until the minimum or average distance $D_2$ between the Raman signal-enhancing materials 22 on adjacent protrusions 14 is less than about 5 nanometers. Alternatively, nanocolumns may be formed using processes known in the art, such as those described in Westwater, J. et al., "Growth of Silicon Nanowires Via Gold/Silane Vapor-Liquid-Solid Reaction," JRNL. VACUUM SCIENCE & TECH. B 15 (3): 554-557 May-June 1997, and in Westwater, J. et al., "Control of the Size and Position of Silicon Nanowires Grown Via the Vapor-Liquid-Solid Technique," JAPANESE JRNL. APPLIED PHYSICS, Part 1-Regular Papers Short Notes & Review Papers, 36 (10): 6204-6209 October 1997, the contents of which are incorporated herein by reference.

Figure 10A:
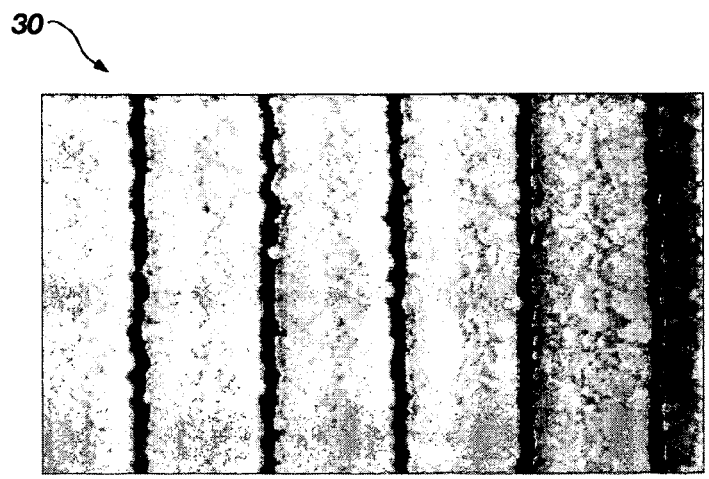
FIGS. 10A-10C are top-view images generated by a scanning electron microscope of a representative NERS-active structure that embodies teachings of the present invention and show one example of a method for depositing Raman signal-enhancing material that embodies teachings of the present invention.
Figure 10B:
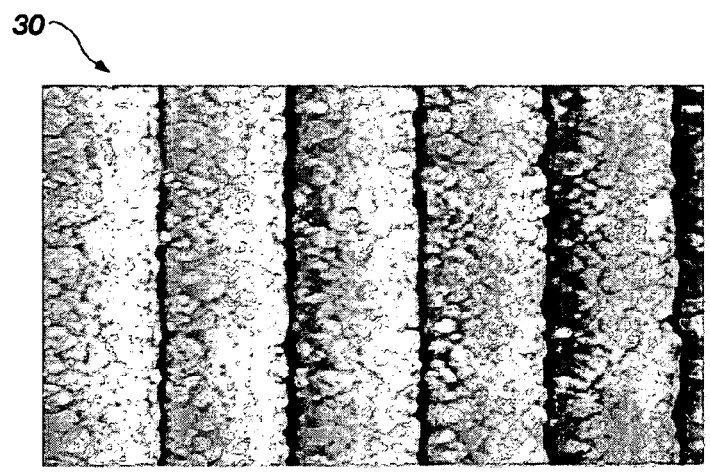
Figure 10C:
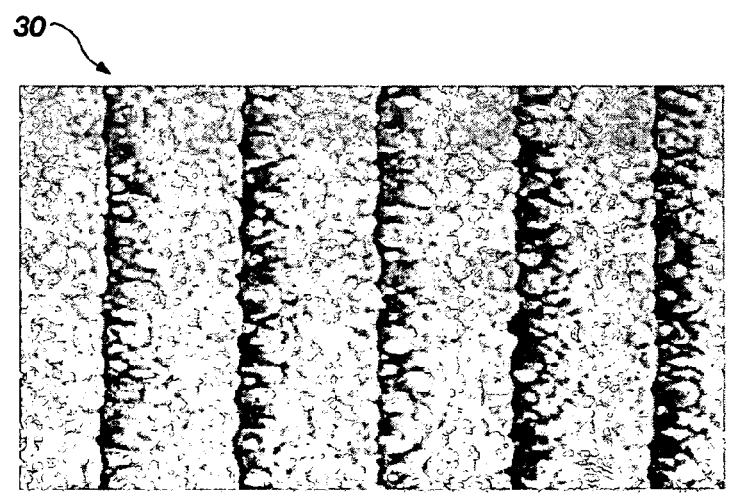

FIGS. 10A-10C are images (generated by a scanning-electron microscope) acquired at various stages of fabrication of a NERS-active structure 30 that embodies representative teachings of the present invention. The NERS-active structure 30 is substantially similar to the idealized NERS-active structure 10, which was previously described with reference to FIGS. 2-3 and FIGS. 9A-9G, and includes Raman signal-enhancing material 22 that is disposed on adjacent protrusions 14 (not visible in FIGS. 10A-10C). FIG. 10A shows the NERS-active structure 30 after applying Raman signal-enhancing material to one side of the protrusions using a shadow deposition process, as described above. FIG. 10B shows the NERS-active structure 30 after applying Raman signal-enhancing material to the other side of the protrusions using a shadow deposition process, as described above. As can be seen by comparing FIG. 10A with FIG. 10B, the average distance separating the Raman signal-enhancing material on adjacent protrusions has been reduced in FIG. 10B relative to FIG. 10A. FIG. 10C shows the NERS-active structure 30 after repeating the above described process to apply another layer of Raman signal-enhancing material to each side of the protrusions. As can be seen by comparing FIG. 10B with FIG. 10C, the average distance separating the Raman signal-enhancing material on adjacent protrusions has been reduced in FIG. 10C relative to FIG. 10B. The above-described process may be repeated any number of times as necessary or desired to provide a selected average distance separating the Raman signal-enhancing material on adjacent protrusions.

As can be seen by comparing FIGS. 10A-10C with FIGS. 2-3, the Raman signal-enhancing material 22 disposed on actual NERS-active structures that embody teachings of the present invention (such as the NERS-active structure 30 shown in FIGS. 10A-10C) may not have a smooth continuous appearance, as illustrated in the idealized representation of the NERS-active structure 10 shown in FIGS. 2 and 3. In contrast, the Raman signal-enhancing material 22 may have a textured, discontinuous appearance, as shown in FIGS. 10A-10C, which may be at least in part to the individual grains of the Raman signal-enhancing material 22 that are grown or formed during the deposition processes.

In yet additional methods, substantially all of the Raman signal-enhancing material may be applied to surfaces of the protrusions in a single step. By way of example and not limitation, a substrate similar to the substrate 42 of the NERS-active structure 40, previously described with reference to FIGS. 4-5, may be provided. The Raman signal-enhancing material 52 may be applied to surfaces of each of the protrusions 44 by establishing a flow of atoms or particles of Raman signal-enhancing material 52 in a direction, and orienting the lateral surfaces of each of the protrusions 44 at an acute angle relative to the direction such that the atoms or particles of Raman signal-enhancing material 52 impinge on at least a portion of the surfaces of the protrusions 44. The substrate 42 and the protrusions 44 then may be rotated about an axis while the Raman signal-enhancing material 52 is being deposited on the protrusions 44, thereby allowing the Raman signal-enhancing material 52 to be deposited on the surfaces of the plurality of protrusions 44 at different angles.

After the Raman signal-enhancing material 22 has been applied to the surfaces 26, 28 of the protrusions 14, the substrate 12, plurality of protrusions 14, and the Raman signal-enhancing material 22 may form a NERS-active structure 10 that embodies teachings of the present invention, as shown in FIG. 9G. The NERS-active structure 10 shown in FIG. 9G may be substantially identical to the NERS-active structure 10 shown in FIGS. 2-3.

NERS-active structures that embody teachings of the present invention, such as, for example, those previously described herein, may be used to provide Raman spectroscopy systems that also embody teachings of the present invention. Such Raman spectroscopy systems may be used to perform Raman spectroscopy according to methods that also embody teachings of the present invention. Such Raman spectroscopy systems and methods for performing Raman spectroscopy are described in further detail below with reference to FIG. 11.

Figure 11:
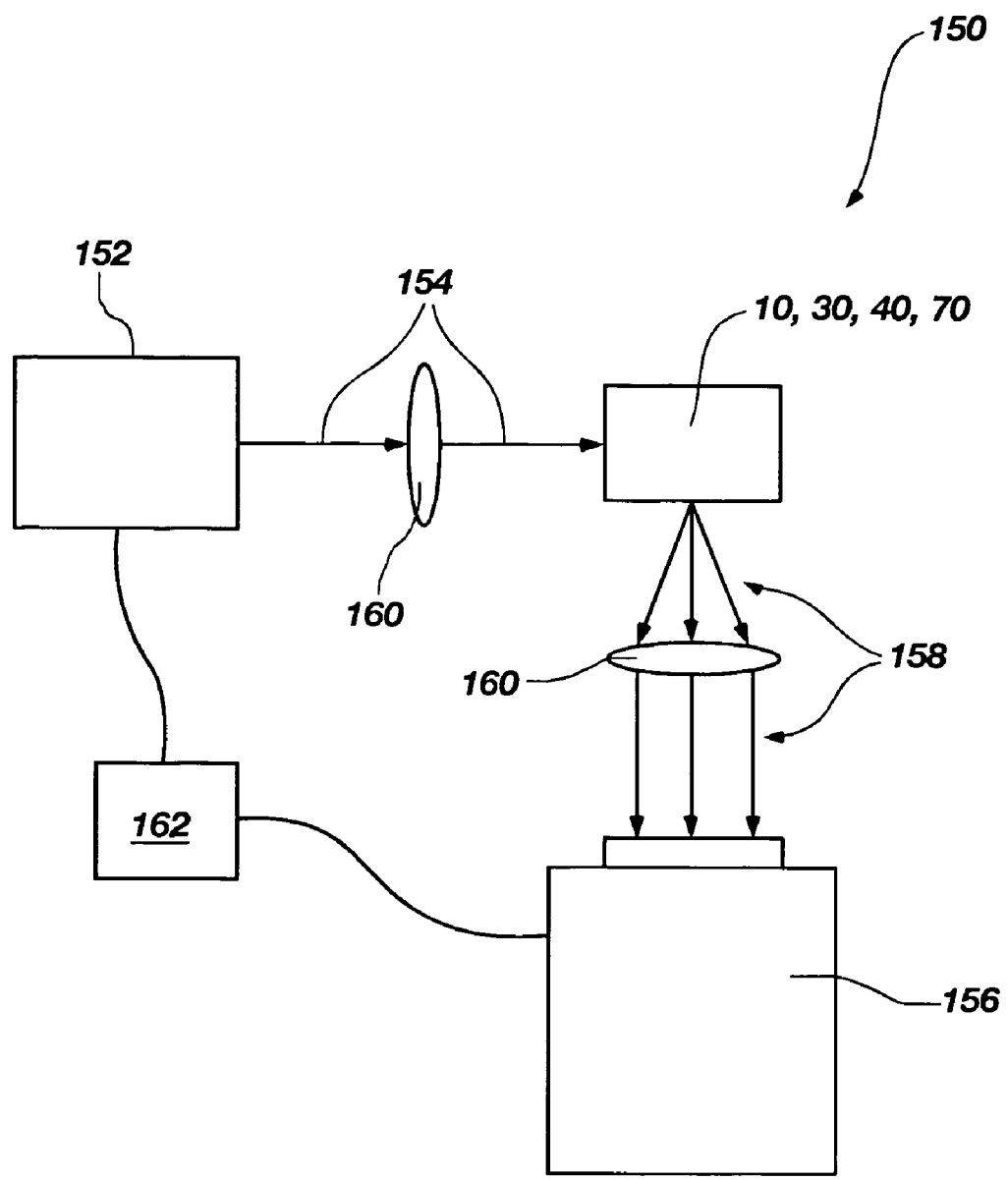
FIG. 11 is a schematic diagram of one example of a Raman spectroscopy system that embodies teachings of the present invention.

FIG. 11 is a schematic diagram of an exemplary Raman spectroscopy system 150 that embodies teachings of the present invention. The Raman spectroscopy system 150 includes an electromagnetic radiation source 152 that is configured to provide incident electromagnetic radiation 154, an electromagnetic radiation detector 156 that is configured to detect Raman scattered radiation 158 that is scattered by an analyte, and a NERS-active structure that embodies teachings of the present invention, such as, for example, the previously described NERS-active structures 10, 30, 40, and 70. The Raman spectroscopy system 150 also may include various optical components 160 (such as, for example, apertures, lenses, and filters) positioned between the electromagnetic radiation source 152 and the NERS-active structure 10, 30, 40, 70 and between the NERS-active structure 10, 30, 40, 70 and the radiation detector 156.

The electromagnetic radiation source 152 may include any suitable source for emitting incident electromagnetic radiation 154 at a desired wavelength, and may be capable of emitting a tunable wavelength of monochromatic incident electromagnetic radiation 154. For example, commercially available semiconductor lasers, helium-neon lasers, carbon dioxide lasers, radiation emitting diodes, incandescent lamps, vertical cavity surface emitting lasers, edge emitting lasers, and many other known radiation emitting sources can be used as the electromagnetic radiation source 152. If necessary, a radiation filter may be used in conjunction with the electromagnetic radiation source 152 to provide monochromatic incident electromagnetic radiation 154. The wavelengths that are emitted by the electromagnetic radiation source 152 may be any suitable wavelength for performing Raman spectroscopy on the analyte, and may be within or near the visible region of the electromagnetic radiation spectrum.

The radiation detector 156 receives and detects the Raman scattered radiation 158 that includes Raman scattered photons that are scattered by an analyte located proximate the NERS-active structure 10, 30, 40, 70. The radiation detector 156 may include a device for determining the wavelength of the Raman scattered radiation 158 and a device for determining the intensity of the Raman scattered radiation 158. By way of example and not limitation, the radiation detector 156 may include a monochromator and a photomultiplier tube. As another example, the radiation detector 156 may include a wavelength dispersive grating and a charge-coupled device (CCD) detector. Typically, the Raman scattered radiation 148 is scattered in all directions relative to the NERS-active structure 10, 30, 40, 70.

Optical components 160 positioned between the electromagnetic radiation source 152 and the NERS-active structure 10, 30, 40, 70 may be used to collimate, filter, or focus the incident electromagnetic radiation 154 before the incident electromagnetic radiation 154 impinges on the NERS-active structure 10, 30, 40, 70 and the analyte. Optical components 160 positioned between the NERS-active structure 10, 30, 40, 70 and the radiation detector 156 can be used to collimate, filter, or focus the Raman scattered radiation 158.

The Raman spectroscopy system 150 also may include a system controller 162 for controlling the radiation source 152, the radiation detector 156, and any controllable components of the NERS-active structure 10, 30, 40, 70. The system controller may include an input system for allowing a user to control the operation of the components of the Raman spectroscopy system 150, and an output system for displaying or otherwise conveying information obtained from the Raman scattered radiation 158. The system controller 162 may be or include a computer device (such as, for example, a desktop or laptop computer or a programmable logic controller) having a signal processor in electrical communication with a memory device. The system controller 162 may be used for collecting, storing, and otherwise manipulating data relating to the Raman signal obtained from the radiation detector 156.

It should be understood that Raman spectroscopy systems that embody teachings of the present invention may be provided in many forms, such as, for example, conventional table top systems or small portable Raman spectroscopy systems. For example, a Raman spectroscopy system that embodies teachings of the present invention may include a probe comprising the previously described NERS-active structure 10, 30, 40, 70. Fiber optic cables or wires may be used to transport the incident electromagnetic radiation 154 from the radiation source 154 to the probe and to deliver Raman scattered radiation 158 from the probe to the radiation detector 156. The radiation source 152 and the radiation detector 156 may be provided in a single portable unit to provide a relatively small, portable Raman spectroscopy system.

To perform Raman spectroscopy using the Raman spectroscopy system 150, an analyte may be provided adjacent the NERS-active structure 10, 30, 40, 70. The NERS-active structure 10, 30, 40, 70 and the analyte then may be irradiated with incident electromagnetic radiation 154 provided by the source 152. Raman scattered radiation 158 that is scattered by the analyte may be detected using the detector 156. The nanostructure 10, 30, 40, 70 may enhance the intensity of the Raman scattered radiation 158, as previously discussed. The wavelengths and corresponding intensity of the Raman scattered radiation 158 may then be determined and used to identify or provide information about the particular analyte.

The structures, systems, and methods described herein may be used to improve the sensitivity of currently available Raman spectroscopy systems and to improve known techniques for performing Raman spectroscopy. Furthermore, at least one of the intensity, uniformity, and homogeneity of a Raman signal emitted by an analyte may be enhanced using the structures, systems, and methods described herein. The methods described herein may be used to provide NERS-active structures that include a small, well controlled, and generally uniform spacing or separation between structures comprising a Raman-signal enhancing material. Furthermore, the NERS-active structures and Raman spectroscopy systems described herein may be used to perform hyper-Raman spectroscopy and to enhance the hyper-Raman scattered radiation. The performance of molecular sensors, nanoscale electronics, optoelectronics, and other devices employing the Raman Effect may be improved by using NERS-active structures, Raman spectroscopy systems, and methods that embody teachings of the present invention.

Although the foregoing description contains many specifics, these are not to be construed as limiting the scope of the present invention, but merely as providing certain representative embodiments. Similarly, other embodiments of the invention can be devised which do not depart from the spirit or scope of the present invention. The scope of the invention is, therefore, indicated and limited only by the appended claims and their legal equivalents, rather than by the foregoing description. All additions, deletions, and modifications to the invention, as disclosed herein, which fall within the meaning and scope of the claims, are encompassed by the present invention.

What is claimed is:

1. A NERS-active structure comprising:
   a plurality of protrusions extending from a surface of a substrate, the plurality of protrusions comprising a first protrusion and a second protrusion; and
   a Raman signal-enhancing material disposed on at least one surface of the first protrusion and at least one surface of the second protrusion, the Raman signal-enhancing material disposed on the first protrusion projecting laterally in a direction generally towards the second protrusion, the Raman signal-enhancing material disposed on the second protrusion projecting laterally in a direction generally towards the first protrusion, at least a portion of the Raman signal-enhancing material projecting from the first protrusion and at least a portion of the Raman signal-enhancing material projecting from the second protrusion being separated by a distance of less than about 10 nanometers.

2. The NERS-active structure of claim 1, wherein the plurality of protrusions are disposed in a periodic array on the surface of the substrate.

3. The NERS-active structure of claim 1, wherein the plurality of protrusions comprise a plurality of nanolines, each nanoline extending substantially parallel to one another laterally along a substantially planar surface of the substrate.

4. The NERS-active structure of claim 1, wherein the plurality of protrusions comprise a plurality of nanocolumns, each nanocolumn extending from a substantially planar surface of the substrate in a direction generally perpendicular to the substantially planar surface of the substrate.

5. The NERS-active structure of claim 1, wherein the Raman signal-enhancing material disposed on the first protrusion comprises a plurality of grains of Raman signal-enhancing material each projecting from the first protrusion, and wherein the Raman signal-enhancing material disposed on the second protrusion comprises a plurality of grains of Raman signal-enhancing material each projecting from the second protrusion.

6. The NERS-active structure of claim 1, wherein the shortest distance between the Raman signal-enhancing material extending from the first protrusion and the Raman signal enhancing material extending from the second protrusion is less than about 5 nanometers.

7. The NERS-active structure of claim 1, wherein the Raman signal-enhancing material comprises a metal.

8. The NERS-active structure of claim 7, wherein the Raman signal-enhancing material comprises at least one of gold, silver, and copper.

9. A method of forming a NERS-active structure, the method comprising:
providing a substrate having a plurality of protrusions extending from a surface of the substrate, the plurality of protrusions including a first protrusion and a second protrusion;
applying Raman signal-enhancing material to at least one surface of the first protrusion, the Raman signal-enhancing material projecting in a lateral direction relative to the surface of the substrate generally towards the second protrusion;
applying Raman signal-enhancing material to at least one surface of the second protrusion, the Raman signal-enhancing material projecting in a lateral direction relative to the surface of the substrate generally towards the first protrusion; and
causing at least a portion of the Raman signal-enhancing material on the at least one surface of the first protrusion to be separated from at least a portion of the Raman signal-enhancing material on the at least one surface of the second protrusion by a distance of less than about 10 nanometers.

10. The method of claim 9, wherein providing a substrate comprises forming the plurality of protrusions on or in the surface of the substrate.

11. The method of claim 10, wherein forming the plurality of protrusions comprises using nanoimprint lithography to form the plurality of protrusions on or in the surface of the substrate.

12. The method of claim 9, wherein applying Raman signal-enhancing material to at least one surface of the first protrusion and applying Raman signal-enhancing material to at least one surface of the second protrusion each comprise exposing the first protrusion and the second protrusion to a flow of atoms or particles of Raman signal-enhancing material.

13. The method of claim 12, wherein applying Raman signal-enhancing material to at least one surface of the first protrusion comprises orienting the at least one surface of the first protrusion at a first acute angle relative to a general direction of the flow of atoms or particles of Raman signal-enhancing material.

14. The method of claim 13, wherein orienting the at least one surface of the first protrusion at a first acute angle comprises causing the first protrusion to shield at least a portion of the second protrusion from the flow of atoms or particles of Raman signal-enhancing material.

15. The method of claim 13, wherein applying Raman signal-enhancing material to at least one surface of the second protrusion comprises orienting the at least one surface of the second protrusion at a second acute angle relative to a general direction of the flow of atoms or particles of Raman signal-enhancing material.

16. The method of claim 15, wherein orienting the at least one surface of the second protrusion at a second acute angle comprises causing the second protrusion to shield at least a portion of the first protrusion from the flow of atoms or particles of Raman signal-enhancing material.

17. The method of claim 9, wherein applying Raman signal-enhancing material to at least one surface of the first protrusion and applying Raman signal-enhancing material to at least one surface of the second protrusion each comprise depositing metal using at least one of a thermal evaporation process, an electron beam evaporation process, an electroless deposition process, and an atomic layer deposition process.

18. A Raman spectroscopy system comprising:
a radiation source;
a nano-enhanced Raman spectroscopy active structure comprising:
a plurality of protrusions extending from a surface of a substrate, the plurality of protrusions comprising a first protrusion and a second protrusion; and
a Raman signal-enhancing material disposed on at least one surface of the first protrusion and at least one surface of the second protrusion, the Raman signal-enhancing material disposed on the first protrusion projecting laterally in a direction generally towards the second protrusion, the Raman signal-enhancing material disposed on the second protrusion projecting laterally in a direction generally towards the first protrusion, at least a portion of the Raman signal-enhancing material projecting from the first protrusion and at least a portion of the Raman signal-enhancing material projecting from the second protrusion being separated by a distance of less than about 10 nanometers; and
a radiation detector configured to detect Raman scattered radiation.

19. The Raman spectroscopy system of claim 18, wherein the radiation source comprises a laser.

20. The Raman spectroscopy system of claim 18, wherein the radiation detector comprises a wavelength dispersive grating and a charge coupled array device.

21. The Raman spectroscopy system of claim 18, wherein the plurality of protrusions are disposed in a periodic array on the surface of the substrate.

22. The Raman spectroscopy system of claim 18, wherein the plurality of protrusions comprise a plurality of nanolines, each nanoline extending substantially parallel to one another laterally along a substantially planar surface of the substrate.

23. The Raman spectroscopy system of claim 18, wherein the plurality of protrusions comprise a plurality of nanocolumns, each nanocolumn extending from a substantially planar surface of the substrate in a direction generally perpendicular to the substantially planar surface of the substrate.

24. The Raman spectroscopy system of claim 18, wherein the Raman signal-enhancing material disposed on the first protrusion comprises a plurality of grains of Raman signal-enhancing material each projecting from the first protrusion, and wherein the Raman signal-enhancing material disposed on the second protrusion comprises a plurality of grains of Raman signal-enhancing material each projecting from the second protrusion.

25. The Raman spectroscopy system of claim 18, wherein the shortest distance between the Raman signal-enhancing material extending from the first protrusion and the Raman signal enhancing material extending from the second protrusion is less than about 5 nanometers.

26. A method of performing Raman spectroscopy on an analyte, the method comprising:
providing a NERS-active structure comprising:
a plurality of protrusions extending from a surface of a substrate, the plurality of protrusions comprising a first protrusion and a second protrusion; and
a Raman signal-enhancing material disposed on at least one surface of the first protrusion and at least one surface of the second protrusion, the Raman signal-enhancing material disposed on the first protrusion projecting laterally in a direction generally towards the second protrusion, the Raman signal-enhancing material disposed on the second protrusion projecting laterally in a direction generally towards the first protrusion, at least a portion of the Raman signal-enhancing material projecting from the first protrusion and at least a portion of the Raman signal-enhancing material projecting from the second protrusion being separated by a distance of less than about 10 nanometers;
providing an analyte proximate the NERS-active structure;
irradiating the analyte with electromagnetic radiation; and
detecting Raman scattered radiation that is scattered by the analyte.

27. The method of claim 26, wherein providing an analyte proximate the NERS-active structure comprises providing an analyte between at least a portion of the Raman signal-enhancing material disposed on the first protrusion and at least a portion of the Raman signal-enhancing material disposed on the second protrusion.

28. The method of claim 26, wherein irradiating the analyte with electromagnetic radiation comprises irradiating the analyte with substantially monochromatic radiation.

\* \* \* \* \*